US008841310B2

(12) United States Patent
Stoffels

(10) Patent No.: US 8,841,310 B2
(45) Date of Patent: Sep. 23, 2014

(54) COMBINATIONS OF A PYRIMIDINE CONTAINING NNRTI WITH RT INHIBITORS

(75) Inventor: Paul Stoffels, Hoogstraten (BE)

(73) Assignee: Janssen R & D Ireland, Eastgate Village, Eastgate Little Island, Co. Cork (IE)

(*) Notice: Subject to any disclaimer, the term of this patent is extended or adjusted under 35 U.S.C. 154(b) by 462 days.

(21) Appl. No.: 12/574,881

(22) Filed: Oct. 7, 2009

(65) Prior Publication Data
US 2010/0029591 A1 Feb. 4, 2010

Related U.S. Application Data

(63) Continuation of application No. 10/570,228, filed as application No. PCT/EP2004/052028 on Sep. 3, 2004, now abandoned.

(60) Provisional application No. 60/499,771, filed on Sep. 3, 2003, provisional application No. 60/508,486, filed on Oct. 3, 2003.

(30) Foreign Application Priority Data

Sep. 3, 2003 (EP) .................................... 03103275
Sep. 8, 2003 (EP) .................................... 03103319
Sep. 10, 2003 (EP) .................................... 03103335
Oct. 2, 2003 (EP) .................................... 03103668

(51) Int. Cl.
A61K 31/505 (2006.01)
A61K 31/513 (2006.01)
A61K 31/52 (2006.01)

(52) U.S. Cl.
CPC ............... A61K 31/505 (2013.01); A61K 31/52 (2013.01); A61K 31/513 (2013.01)
USPC .......... 514/256; 514/81; 514/274; 514/263.4; 514/269; 514/252.02; 514/252.03; 514/255.05; 514/247; 514/252.06; 544/319; 544/238; 544/239

(58) Field of Classification Search
CPC .... A61K 31/52; A61K 31/505; A61K 31/513
USPC ........... 514/256, 81, 274, 263.4, 269, 252.02, 514/252.03, 255.05, 247
See application file for complete search history.

(56) References Cited

U.S. PATENT DOCUMENTS

| | | | |
|---|---|---|---|
| 5,182,111 A | 1/1993 | Aebischer et al. |
| 5,368,864 A | 11/1994 | Lahr et al. |
| 5,705,270 A | 1/1998 | Soon-Shiong et al. |
| 6,221,400 B1 | 4/2001 | Liversidge et al. |
| 2001/0026804 A1 | 10/2001 | Boutignon |
| 2002/0009493 A1 | 1/2002 | Schwendeman et al. |
| 2004/0082937 A1 | 4/2004 | Ausiello et al. |
| 2004/0115268 A1 | 6/2004 | Ashton et al. |
| 2004/0198739 A1 | 10/2004 | Guillemont et al. |
| 2005/0163855 A1 | 7/2005 | Cho et al. |
| 2006/0269475 A1 | 11/2006 | Ryu et al. |
| 2008/0081064 A1 | 4/2008 | Jelle et al. |
| 2011/0257111 A1 | 10/2011 | Harbeson et al. |

FOREIGN PATENT DOCUMENTS

| | | |
|---|---|---|
| EP | 0 489 181 A1 | 10/1996 |
| EP | 0 499 299 B1 | 8/2000 |
| EP | 1 350 792 A1 | 10/2003 |
| EP | 1 214 059 B1 | 5/2005 |
| EP | 1 632 232 A1 | 3/2006 |
| JP | 06-316524 | 11/1994 |
| WO | WO 93/23021 A2 | 11/1993 |
| WO | WO 96/01110 A2 | 1/1996 |
| WO | WO 01/74329 A2 | 10/2001 |
| WO | WO 02/30482 A1 | 4/2002 |
| WO | WO 03/000235 A1 | 1/2003 |
| WO | WO 03/016306 A1 | 2/2003 |
| WO | WO 03/043586 A2 | 5/2003 |
| WO | WO 2004/016581 A1 | 2/2004 |
| WO | WO 2004/043433 A2 | 5/2004 |
| WO | WO 2004/046143 A1 | 6/2004 |
| WO | WO 2004/050058 A2 | 6/2004 |
| WO | WO 2004/069812 A1 | 8/2004 |
| WO | WO 2005/021001 A1 | 3/2005 |
| WO | WO 2005/123076 A2 | 12/2005 |
| WO | WO 2006/024668 A1 | 3/2006 |
| WO | WO 2006/026500 A1 | 3/2006 |
| WO | WO 2006/055603 A2 | 5/2006 |
| WO | WO 2006/106103 A2 | 10/2006 |
| WO | WO 2006/108828 A1 | 10/2006 |
| WO | WO 2006/131806 A2 | 12/2006 |
| WO | WO 2007/014393 A2 | 2/2007 |
| WO | WO 2007/082922 A2 | 7/2007 |
| WO | WO 2007/147882 A3 | 12/2007 |
| WO | WO 2008/110619 A1 | 6/2008 |
| WO | WO 2009/007441 A3 | 1/2009 |
| WO | WO 2009/046299 A3 | 4/2009 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Rosenbach et al, (Clinical infectious disease, vol. 34 (5), 2002, pp. 686-692.*

(Continued)

Primary Examiner — Savitha Rao
(74) Attorney, Agent, or Firm — Kirk Baumeister

(57) ABSTRACT

The present invention concerns combinations of a pyrimidine containing NNRTI with nucleoside reverse transcriptase inhibitors and/or nucleotide reverse transcriptase inhibitors useful for the treatment of HIV infected patients or for the prevention of HIV transmission or infection.

33 Claims, No Drawings

(56) References Cited

OTHER PUBLICATIONS

Arimilli, M.N., et al. "Synthesis, in vitro Biological Evaluation and Oral Bioavailability of 9-[2-(phosphonomethoxy)propyl]adenine (PMPA) Prodrugs", Antibiral Chemistry & Chemotherapy (1977) 8(6): 557-564.
Clercq, E., "Perspectives of Non-Nucleoside Reverse Transcriptase Inhibitors (NNRTIs) The Therapy of HIV-1 Infection", Farmaco 54 (1999) pp. 26-45.
Gilead (XP002314669) Press Release Study 934 (2005).
Gulick, R. M., "New Antiretroviral Drugs", Clinical of Microbiological Infections (2003) 9 pp. 186-193.
Harrer, E., et al. "Recognition of the Highly Conserved YMDD Region in the Human Immunodeficiency Virus Type 1 Reverse Transcriptase by HLA-A2-Restricted Cytotoxic T Lymphocytes From an Asymptomatic Long-Term Nonprogressor", Journal of Infectious Diseases (1996) pp. 476-479.
Hazen, R., et al., Relative Anti-HIV-1 Efficacy of Lamivudine and Emtricitabine in Vitro is Dependent on Cell Type, Journal of Acquired Immune Deficiency Syndromes, (2003) pp. 255-258.
Hoong, L., et al. "Enzyme-Mediated Enantioselective Preparation of Pure Enantiomers of the Antiviral Agent 2',3'-Dideoxy-5-Fluoro-3'-Thiacytidine (FTC) and Related Compounds", J. Organic Chemistry (1992) pp. 5563-5565.
Jeong, L., et al. "Asymmetric Synthesis and Biological Evaluation of β-L-(2R,5S)- and α-L-(2R,5R)-1,3-Oxathiolane-Pyrimidine and -Purine Nicleosides as Potential Anti-HIV Agents", Journal of Medicinal Chemistry, (1993) vol. 36(2) pp. 181-195.
Kumar, P., et al. "Safety and Pharmacokinetics of Abacavir (159U89) Following Oral Administration of Escalating Single Doses in Immunodeficiency Virus Type 1-Infected Adults", Antimicrobial Agents and Chemotherapy (1999) pp. 603-608.
Otten, R., et al. "Efficacy of Postexposure Prophylaxis After Intravaginal Exposure of Pig-Tailed Macaques to a Human-Derived Retrovirus (Human Immunodeficiency Virus Type 2)", Journal of Virology (2000) pp. 9771-9775.
Pavia, A., "Abacavir/Lamivudine in Combination With Efavirenz, Amprenavir/Ritonavir or Staviduinen", XP-002274550, the XIV International AIDS Conference (2005).
Peiperl, L., et al., Tenofovir (Viread PMPA), Drug overview, Aug. 7, 2003.
Perno, C., et al. "Potent Inhibition of Human Immunodeficiency Virus and Herpes Simplex Virus Type 1 by 9-(2-Phosphonylmethoxy-ethyl)adenine in Primary Macrophages is Determined by Drug Metabolism, Nucleotide Pools, and Cytokines", Molelcular Pharmacology (1996) pp. 359-366.
Perno, C., et al. "Different Pattern of Activity of Inhibitors of the Human Immunodeficiency Virus in Lymphocytes and Monocyte/Macrophages", Antiviral Research (1992) pp. 389-304.
Young, B., "Can Abacavir Be Given Once-A-Day?" XP-002274551, the 43rd Interscience Conference on Antimicrobial Agents and Chemotherapy (2005).
Miller et al., Interscience Conference on Antimicrobial Agents and Chemotherapy (1998).
Hayashi, et al., "Characterization of inhibitory action of concanamycins against herpes simplex virus", Antiviral Chemistry & Chemotherapy, (2001) pp. 51-59, vol. 12, International Medical Press.
Fridland, et al., Antiviral Research (1997), 34.
Van Roey, P., et al., "Absolute configuration of the antiviral agent (−)-cis-5-fluoro-1-[2-hydroxymethyl)-1.3-oxathiolan-5-yl]cytosine", Antiviral Chemistry & Chemotherapy (1993), pp. 369-375, vol. 4, issue 6.
Tisdale, et al., Antiviral Research (1993), 20:Suppl 1.
Lanier, et al., International Conference on Retroviruses and Opportunistic Infections (1998).
Robbins, B., et al. "Metabolic Pathways for Activation of the Antiviral Agent 9-(2-Phosphonylmethoxyethyl)Adenine in Human Lymphoid Cells", Antimicorbial Agents and Chemotherapy (1995) pp. 2304-2308.
Robbins, B., et al. Anti-Human Immunodeficiency Virus Activity and Cellular Metabolism of a Potential Prodrug of the Acyclic Nucleoside Phosphonate 9-R-(2-Phosphonomethoxpropyl)adenine (PMPA), Bis(isopropyloxymethlycarbonyl)PMPA, Antimicrobial Agents and Chemotherapy (1998) pp. 612-617.
Schinazi, R., et al. "Selective Inhibition of Human Immunodeficiency Viruses by Racemates and Enantiomers of cis-5-Fluoro-1-[2-(Hydroxymethly)-1,3-Oxathiolan-5-yl]Cytosine", Antimicrobial Agents and Chemotherapy (1992) pp. 2423-2431.
Schinazi, R., et al. "Characterization of Human Immunodeficiency Viruses Resistant to Oxathiolane-Ctosine Nucleosides" Antimicrobial Agents and Chemotherapy (1993) pp. 875-881.
Smith, R., et al. "A Novel Met-to-Thr Mutation in the YMDD Motif of Reverse Transcriptase from Feline Immunodeficiency Virus Confers Resistance to Oxathiolane Nucleosides", Journal of Virology (1997) pp. 2357-2362.
Squires, K., et la. "An Introduction of Nucllleoside and Nucleotide Analogues", XP009042950, Antiviral Therapy 6 (2001) pp. 1-14.
Suo, et al., "Selective Inhibition of HIV-1 Reverse Transcriptase by an Antiviral Inhibitor, (R)-9-(2-Phosphonylmethoxypropyl)adenine" (1998) pp. 27250-27258, vol. 273, issue 42, The Journal of Biological Chemistry.
Tisdale, M., et al. "Rapid in vitro Selection of Human Immunodeficiency virus type 1 Resistant to 3'-thiacytidine Inhibitors Due to a Mutation in the YMDD Region of Reverse Transcripase", (1993) pp. 5653-5656.
Van Rompay, K., et al. "9-[2(Phosphonomethoxy)Propyl]Adenine therapy of Established Simian Immunodeficiency Virus Infection in Infant *Rhesus macaques*", Antimicrobial Agents and Chemotherapy (1996) pp. 2586-2591.
Witvrouw, M., et al. "In Virto Evaluation of the Effect of Temporary Removal of HIV Drug Pressure", Antiviral Research (2000) pp. 215-221.
International Search Report dated Feb. 7, 2005 for related International Application No. PCT/EP2004/052028.
Farquhar, et al., "Salivary Secretory Leukocyte Protease Inhibitor Is Associated with Reduced Transmission of Human Immunodeficiency Virus Type 1 Through Breast Milk," The Journal of Infectious Diseases, 186: 1173-1176 (2002).
Janssen, et al., "In Search of a Novel Anti-HIV Drug: Multidisciplinary Coordination in the Discovery of 4-[[4-[[4-(1E)-2-Cyanoethenyl]-2,6-dimethylphenyl]amino]2-pyrimidinyl]amino]benzonitrile (R278474, Rilpivirine)," Journal of Molecular Chemistry, 48: 1901-1909 (2005).
Merisko-Liversridge, et al., "Nanosizing: a formulation approach for poorly-water-soluble compounds," European Journal of Pharmaceutical Science, 18: 113-120 (2003).
McNeely, et al., "Secretory Leukocyte Protease Inhibitor: A Human Saliva Protein Exhibiting Anti-Human Immunodeficiency Virus 1 Activity In Vitro," The Journal of Clinical Investigation, 96: 456-464 (1995).
Müller, et al., "Nanosuspensions as particulate drug formulations in therapy Rationale for development and what we can expect for the future," Advanced Drug Delivery Reviews, 47: 3-19 (2001).
Okwundu, et al., "Antiretroviral pre-exposure prophylaxis (PrEP) for preventing HIV in high-risk individuals," The Cochran Library, 4: 1-23 (2009).
Patel, et al., "Poloxamers: A pharmaceutical excipients with therapeutic behaviors," International Journal of PharmaTech Research, 1(2): 299-303 (2009).
Rabin, et al., "In vitro and in vivo demonstration of risperidone implants in mice," Schizophrenia Research, 98: 66-78 (2008).
Smith, et al., "An assessment of the use of Implanon® in three community services," The Journal of Family Planning and Reproductive Health Care, 28(4): 193-196 (2002).
Susman, et al., Retroviruses and Opportunistic Infections—12th Conference, IDrugs, 8(4): 299-302 (2005).
Wahl, et al., American Journal of Pathology, 150(4): 1275-1284 (1997).
PCT International Search Report in WO 2005/021005 dated Feb. 7, 2005.

(56) References Cited

OTHER PUBLICATIONS

PCT International Search Report in WO 2011/080141 dated Dec. 19, 2011.
Harry G. Brittain, "Polymorphism in Pharmaceutical Solids," Chapter 1, pp. 1-10, 1999.
Harry G. Brittain, "Polymorphism in Pharmaceutical Solids," Chapter 5, pp. 183-226, 1999.
Bryn, et al., "Solid-State Pharmaceutical Chemistry," Chem. Mater., 6: 1148-1158 (1994).
Gregoriadis, et al., "Targeting of Drug 6 Strategies for Stealth Therapeutic Systems," vol. 300, pp. 4-5 (1998).
Guillemont, et al., "Synthesis of Novel Diarylpyrimidine Analogues and their Antiviral Activity against Human Imunodeficiency Virus Type 1," Journal of Medicinal Chemistry, 48: 2072-2079 (2005).
Marcus, et al., "HIV: epidemiology and strategies for therapy and vaccination," Intervirology, 45(4-6): 260-266 (2002). Abstract Only.
Silvestri, et al., "Current state-of-the-art in preclinical and clinical development of novel non-nucleotide HIV-1 reverse transcriptase inhibitors," Expert Opinion on Therapeutic Patents, 16(7): 939-962 (2006) Abstract Only.
Van Heeswijk, et al., "Combination of protease inhibitors for the treatment of HIV-1-infected patients: a review of pharmacokinetics and clinical experience," Antiviral therapies, 6(4): 201-229 (2001).

\* cited by examiner

COMBINATIONS OF A PYRIMIDINE CONTAINING NNRTI WITH RT INHIBITORS

CROSS REFERENCE TO RELATED APPLICATIONS

This application is a continuation of U.S. application Ser. No. 10/570,228, filed Feb. 28, 2006 now abandoned, which in turn is a national stage of PCT Application No. PCT/EP2004/052028, filed Sep. 3, 2004, which claims priority for EPO Patent Application No. 03103275.8, filed Sep. 3, 2003, and EPO Patent Application No. 03103319.4, filed Sep. 8, 2003, and EPO Patent Application No. 03103335.0, filed Sep. 10, 2003 and EPO Patent Application No. 03103668.4, filed Oct. 2, 2003 and U.S. Provisional Application No. 60/499,771, filed Sep. 3, 2003 and U.S. Provisional Application No. 60/508,486, filed Oct. 3, 2003, all of which are hereby incorporated by reference in their entirety.

FIELD OF THE INVENTION

The present invention concerns combinations of a pyrimidine containing NNRTI with nucleoside reverse transcriptase inhibitors and/or nucleotide reverse transcriptase inhibitors useful for the treatment of HIV infected patients or for the prevention of HIV transmission or infection.

BACKGROUND OF THE INVENTION

Despite the fact that significant progress has been made by the introduction of HAART therapy (Highly Active Anti-Retroviral Therapy), resistance of the HIV virus against nucleoside reverse transcriptase inhibitors (NRTIs), non-nucleoside reverse transcriptase inhibitors (NNRTIs), nucleotide reverse transcriptase inhibitors (NtRTIs), protease inhibitors and even the more recent fusion inhibitors is still a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. On the International AIDS Conference in Paris in July 2003, researchers released that the biggest study so far of resistance to AIDS drugs finds that about 10 percent of all newly infected people in Europe have drug-resistant strains. Smaller tests to determine the spread of resistance have been done in the high-risk city center of San Francisco. This test showed the highest level of resistance at 27 percent.

The pharmacokinetic profile of many commercially available antiretrovirals does not allow relatively low therapeutic doses. Poor pharmacokinetic profiles often in combination with poor solubility properties of the antiretrovirals cause the AIDS patient to face a high pill burden which is particularly undesirable for drug-naïve patients or first line therapy. Moreover, as a consequence of the AIDS virus even resisting antiretroviral combination therapy, a physician will boost the plasma levels of the active drugs in order for said antiretrovirals to regain effectivity against the mutated HIV viruses, the consequence of which is an even higher increase in pill burden. Boosting plasma levels may also lead to an increased risk of non-compliance with the prescribed therapy and to increased side-effects.

Several attempts have been made to date to design combination regimens. For instance, the combination of lamivudine (a nucleoside RT inhibitor also named 3TC) at a 150 mg dose and zidovudine (a nucleotide RT inhibitor also named AZT) at a 300 mg dose, formulated in an oral tablet and dosed twice daily, or the combination of abacavir sulfate at a dose equivalent to 300 mg abacavir (a nucleoside RT inhibitor), lamivudine at a 150 mg dose and zidovudine at a 300 mg dose, formulated in an oral tablet and dosed twice daily.

WO 93/23021 describes therapeutic combinations for the treatment of HIV-infections comprising zidovudine and an agent serving to enhance the antiviral activity against HIV populations otherwise resistant to zidovudine.

WO 96/01110 describes a triple combination of zidovudine, lamivudine and loviride, the latter being a non-nucleoside RT inhibitor of the α-APA class.

An overview of new antiretroviral drugs is given in *Clinical Microbiology and Infection* 2003, Vol. 9: 3, pp. 186-193.

WO 03/016306 specifically discloses more than 250 pyrimidine derivative having HIV replication inhibiting properties that act as non-nucleoside RT inhibitors (NNRTIs) having the ability to inhibit the replication both wild-type and of mutant strains. One of said NNRTIs is 4-[[4-[[4-(2-cyanoethenyl)-2,6-dimethylphenyl]-amino]-2-pyrimidinyl]amino]-benzonitrile (herein referred to as TMC278). WO 03/016306 also discloses the methods to synthesize these compounds. It further discloses combinations of said NNRTIs with other antiretrovirals, i.e. suramine, pentamidine, thymopentin, castanospermine, dextran (dextran sulfate), foscarnet-sodium (trisodium phosphono formate), zidovudine (3'-azido-3'-deoxythymidine, AZT), didanosine (2',3'-di-deoxyinosine; ddI), zalcitabine (dideoxycytidine, ddC), lamivudine (2'-3'-dideoxy-3'-thiacytidine, 3TC), stavudine (2',3'-didehydro-3'-deoxythymidine, d4T), abacavir, nevirapine (11-cyclopropyl-5,11-dihydro-4-methyl-6H-dipyrido-[3,2-b: 2',3'-e][1,4]diazepin-6-one), efavirenz, delavirdine, TMC120, TMC125, tenofovir, (S)-8-chloro-4,5,6,7-tetrahydro-5-methyl-6-(3-methyl-2-butenyl)imidazo-[4,5,1-jk][1,4]benzodiazepine-2 (1H)-thione, α-[(2-nitrophenyl)amino]-2,6-dichloro-benzene-acetamide, RO-5-3335, indinavir, ritonavir, saquinavir, lopinavir (ABT-378), nelfinavir, amprenavir, TMC126, BMS-232632, VX-175, T-20, T-1249, AMD-3100 and hydroxyurea.

Notwithstanding existing combination therapy, there is still a need for improved antiretroviral therapy, more particularly AIDS therapy. This need is particularly acute for therapy that is effective not only on wild type HIV virus, but also on the increasingly more common resistant HIV viruses. It is thus highly desirable especially for first line therapy to design a combination regimen with a low pill burden that limits or even suppresses the recurrence of drug resistant virus and which can be used and remains effective for a long term.

It is an object of the invention to provide combinations of more than one therapeutically effective antiretroviral drug, which combinations can be used as first line therapy in drug-naïve patients for a long period of time.

It is also an object of the invention to provide combinations of more than one therapeutically effective antiretroviral drug in which the antiretroviral drugs have a complementary resistance profile thus creating a high resistance barrier and thus allowing a drug-naïve patient to take the combinations for a long period of time.

Another object of the invention is to provide combinations of more than one therapeutically active antiretroviral drug wherein each of the active antiretroviral drugs of the combinations can be administered once daily thus reducing the pill burden for the patient.

A further object of the invention is to provide combinations of more than one therapeutically active antiretroviral drug wherein each of the active antiretroviral drugs of the combinations can be co-formulated.

Yet a further object of the invention is to provide combinations of more that one therapeutically active antiretroviral drug wherein a therapeutically effective amount of each of the active antiretroviral drugs of the combinations can be co-formulated in one single pharmaceutical formulation.

Another object of the present invention is to provide combinations of more than one active antiretroviral drug which combinations can be used to prevent HIV transmission or infection in humans.

All references cited herein are incorporated by reference.

SUMMARY OF THE INVENTION

Thus in a first aspect, the present invention provides a combination comprising (i) TMC278 or a stereoisomeric form thereof; or a pharmaceutically acceptable salt thereof; or a prodrug thereof; and (ii) a nucleoside reverse transcriptase inhibitor and/or a nucleotide reverse transcriptase inhibitor; wherein TMC278 and the nucleotide reverse transcriptase inhibitor and/or the nucleoside reverse transcriptase inhibitor are therapeutically effective HIV inhibitors at a dose that can be administered once daily.

Thus in a second aspect, the present invention provides a combination comprising (i) TMC278 or a stereoisomeric form thereof; or a pharmaceutically acceptable salt thereof; or a prodrug thereof; and (ii) a nucleoside reverse transcriptase inhibitor; wherein TMC278 and the nucleoside reverse transcriptase inhibitor are therapeutically effective HIV inhibitors at a dose that can be administered once daily.

In a third aspect there is provided a combination comprising (i) TMC278 or a stereoisomeric form thereof; or a pharmaceutically acceptable salt thereof; or a prodrug thereof; and (ii) a nucleotide reverse transcriptase inhibitor; wherein TMC278 and the nucleotide reverse transcriptase inhibitor are therapeutically effective HIV inhibitors at a dose that can be administered once daily.

In a fourth aspect there is provided a triple combination comprising (i) TMC278 or a stereoisomeric form thereof; or a pharmaceutically acceptable salt thereof; or a prodrug thereof; and (ii) a nucleoside reverse transcriptase inhibitor; and (iii) a nucleotide reverse transcriptase inhibitor; wherein TMC278 and the nucleotide reverse transcriptase inhibitor and the nucleoside reverse transcriptase inhibitor are therapeutically effective HIV inhibitors at a dose that can be administered once daily.

In a fifth aspect there is provided a triple combination comprising (i) TMC278 or a stereoisomeric form thereof; or a pharmaceutically acceptable salt thereof; or a prodrug thereof; and (ii) a nucleoside reverse transcriptase inhibitor; and (iii) a second nucleoside reverse transcriptase inhibitor different from the nucleoside reverse transcriptase inhibitor of (ii); wherein TMC278 and the first and second nucleoside reverse transcriptase inhibitors are therapeutically effective HIV inhibitors at a dose that can be administered once daily.

In another aspect there is provided a pharmaceutical formulation comprising a pharmaceutically acceptable carrier and a combination as specified herein.

The invention also concerns the use of the combinations specified herein as HIV inhibitors and the use thereof in the treatment of HIV infected patients or in the prevention of HIV transmission or infection.

The invention is based on the finding that TMC278 is a potent reverse transcriptase inhibitor that has an extremely high genetic barrier in combination with a favourable pharmacokinetic profile allowing once daily dosing. It was surprising to discover that TMC278 has all these properties together. This is unusual because one cannot predict what mutations will be selected in the HIV-1 genome by a given drug, whether the mutated virus will have any chance of survival under the pressure of the drug, how much drug is needed to limit or to suppress the recurrence of such mutated virus, and at what frequency such drug has to be given to maintain suppression of the development of a resistant virus that can break through the genetic barrier of the drug.

DETAILED DESCRIPTION OF THE INVENTION

As used herein the term 'therapeutically effective HIV inhibitors at a dose that can be administered once daily' means that the HIV inhibitors are suitable for dosing every 24 hours. The 'term suitable for dosing every 24 hours' means that the HIV inhibitors are such that they can be administered every 24 hours and give effective blood plasma concentrations of the active ingredients such that they are effective to suppress HIV infection over a period of 24 hours. The HIV inhibitors for use in the invention can be dosed every 24 hours.

TMC278 or 4-[[4-[[4-(2-cyanoethenyl)-2,6-dimethylphenyl]-amino]-2-pyrimidinyl]-amino]-benzonitrile is a known NNRTI, which can be prepared as described in WO03/016306. TMC278 can be used in base form or, which is preferred, as a suitable pharmaceutically acceptable salt form, in particular as an acid addition salt form. The pharmaceutically acceptable addition salts are meant to comprise the therapeutically active non-toxic salt forms. The acid addition salt forms can be obtained by treating the base form with appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxy-propanoic, 2-oxopropanoic, oxalic, malonic, succinic, maleic, fumaric, malic, tartaric, 2-hydroxy-1,2,3-propanetricarboxylic, methanesulfonic, ethanesulfonic, benzene-sulfonic, 4-methylbenzenesulfonic, cyclohexanesulfamic, 2-hydroxybenzoic, 4-amino-2-hydroxybenzoic and the like acids. Preferred for use in the present invention are the hydrohalic acid salts, in particular the hydrochloride salt.

TMC278 occurs in stereoisomeric forms, more in particular as E- and Z-isomeric forms. Both isomers may be used in the combinations of the present invention. Whenever reference is made herein to TMC278, the E- and the Z-form as well as any mixture of both forms are meant to be included.

A preferred form of TMC278 for use in the invention is the E-isomer, i.e. (E)-4-[[4-[[4-(2-cyanoethenyl)-2,6-dimethylphenyl]-amino]-2-pyrimidinyl]-amino]-benzonitrile (hereinafter called E-TMC278). The Z-isomer of TMC278, i.e. (Z)-4-[[4-[[4-(2-cyanoethenyl)-2,6-dimethylphenyl]-amino]-2-pyrimidinyl]-amino]-benzonitrile (hereinafter called compound Z-TMC278) can also be used. It has relatively high potency against wild-type HIV-1 but is less active against single and double mutants in comparison to the E-isomer. Table 1 shows the $IC_{50}$ value in mM of the E and Z-isomer of TMC278.

TABLE 1

| HIV RT mutation | E-isomer | Z-isomer |
|---|---|---|
| Wild-type | 0.4 | 0.6 |
| 100I | 0.4 | 6.3 |

TABLE 1-continued

| HIV RT mutation | E-isomer | Z-isomer |
|---|---|---|
| 103N | 0.3 | 1.6 |
| 181C | 1.3 | 5.0 |
| 188L | 2,0 | 32 |
| 227C | 2.0 | 4.0 |
| 100I + 103N | 7.9 | 790 |
| 103N + 181C | 1.0 | 40 |
| 227L + 106A | 1.0 | 4.0 |

Whenever reference is made herein to the E-form of TMC278 (i.e. E-TMC278), the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of TMC278 (i.e. Z-TMC278), the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. Of particular interest is the Z-form substantially free of the E-form. Substantially free in this context refers to E-Z-mixtures with no or almost no E-form, e.g. isomeric mixtures containing as much as 90%, in particular 95% or even 98% or 99% of the Z-form.

Also meant to be included for use in this invention are salts of the isomeric forms of TMC278, in particular the salts mentioned above. Of particular interest are Z-TMC278 hydrochloride and specifically E-TMC278 hydrochloride.

Advantageously, the nucleotide reverse transcriptase inhibitor and the nucleoside reverse transcriptase inhibitor select mutations in the reverse transcriptase that do not cause resistance to TMC278. Of particular interest therefore is any combination specified herein wherein (1) TMC278 and the nucleoside/nucleotide reverse transcriptase inhibitor or inhibitors are therapeutically effective HIV inhibitors at a dose that can be administered once daily and (2) the nucleoside/nucleotide reverse transcriptase inhibitor or inhibitors select mutations in the reverse transcriptase that do not cause resistance to TMC278.

Specifically, in one embodiment, a combination is provided comprising (i) TMC278 or its stereoisomeric form or pharmaceutically acceptable salt or its prodrug, and (ii) a nucleoside reverse transcriptase inhibitor, wherein (1) TMC278 and the nucleoside reverse transcriptase inhibitor are therapeutically effective HIV inhibitors at a dose that can be administered once daily and (2) the nucleoside reverse transcriptase inhibitor selects mutations in the reverse transcriptase that do not cause resistance to TMC278. In another embodiment, a combination is provided comprising (i) TMC278 or its stereoisomeric form or pharmaceutically acceptable salt or its prodrug, and (ii) a nucleotide reverse transcriptase inhibitor, wherein (1) TMC278 and the nucleotide reverse transcriptase inhibitor are therapeutically effective HIV inhibitors at a dose that can be administered once daily and (2) the nucleotide reverse transcriptase inhibitor selects mutations in the reverse transcriptase that do not cause resistance to TMC278.

In a preferred embodiment, a triple combination is provided comprising (i) TMC278 or its stereoisomeric form or pharmaceutically acceptable salt or its prodrug, and (ii) a nucleoside reverse transcriptase inhibitor, and (iii) a nucleotide reverse transcriptase inhibitor, wherein (1) TMC278 and the nucleotide reverse transcriptase inhibitor and the nucleoside reverse transcriptase inhibitor are therapeutically effective HIV inhibitors at a dose that can be administered once daily and (2) the nucleotide reverse transcriptase inhibitor and the nucleoside reverse transcriptase inhibitor select mutations in the reverse transcriptase that do not cause resistance to TMC278.

In another preferred embodiment, a triple combination is provided comprising (i) TMC278 or its stereoisomeric form or pharmaceutically acceptable salt or its prodrug, and (ii) a nucleoside reverse transcriptase inhibitor, and (iii) a second nucleoside reverse transcriptase inhibitor different from the nucleoside reverse transcriptase inhibitor of (ii); wherein (1) TMC278 and the nucleoside reverse transcriptase inhibitors are therapeutically effective HIV inhibitors at a dose that can be administered once daily and (2) the nucleoside reverse transcriptase inhibitors select mutations in the reverse transcriptase that do not cause resistance to TMC278.

Preferred nucleotide reverse transcriptase inhibitors that can be used in the combinations subject of this invention include tenofovir and its prodrug tenofovir disoproxil fumarate.

Tenofovir is an adenosine nucleotide analogue currently commercially available with activity against retroviruses. Tenofovir disoproxil fumarate (tenofovir DF) is a once-daily, orally administered prodrug of tenofovir. For antiviral activity, tenofovir DF needs to be hydrolysed to the ANP analogue and then phosphorylated to the active diphosphate moiety [Arimilli et al *Antiviral Chemistry and Chemotherapy* 1997, 8:6 (557-564); Fridland et at. *Antiviral Research* 1997, 34]. After entry in to lymphocytes or macrophages, the prodrug is quantitatively converted to the parent analogue, tenofovir, and phosphorylated to mono- and diphosphate metabolites. The cellular enzymes that are responsible for phosphorylation of this drug are adenylate kinase and nucleoside diphosphate kinase [Robbins et al. *Antimicrobial Agents and Chemotherapy* 1995, 39:10 (2304-2308); Robbins et al. *Antimicrobial Agents and Chemotherapy* 1998, 42:3 (612-617)]. Unlike other nucleoside analogues, such as zidovudine or stavudine, both of whose phosphorylation is cell cycle-dependent, tenofovir is efficiently phosphorylated in resting as well as cycling peripheral blood lymphocytes [Robbins et al. 1998]. Tenofovir can inhibit HIV-1 replication in different cell types that may target HIV, including primary human blood lymphocytes and macrophages [Perno et al. *Antiviral Research* 1992 (289-304); Perno et al. *Molecular Pharmacology* 1996, 50:2 (359-366)]. The primary target of tenofovir diphosphate is reverse transcriptase (RT). Tenofovir diphosphate is a competitive inhibitor for the incorporation of deoxyadenosine triphosphate into nascent proviral DNA chains. Inhibition of HIV-1 RT by tenofovir diphosphate has an inhibition constant of approximately 0.9 μM, and if the analogue is incorporated into the growing viral DNA chain it may terminate further chain elongation. Tenofovir inhibits viral RT much more effectively than it inhibits cellular DNA polymerases [Suo et al *Journal of Biological Chemistry* 1998, 273:42 (2750-2758)]. The concentration required to inhibit the replication of various HIV-1 strains by 50% (EC50) in lymphocyte and macrophage cell types (MT-2, CEM, ACH8) ranges from 0.2 to 10 μM. The antiviral effect is achieved at non-toxic doses of tenofovir (selectivity index ranging from 100 to 2000). Tenofovir DF is currently available as 300 mg tablets to be taken once daily.

Viral resistance to tenofovir in vitro emerges slowly. A recombinant virus expressing the K65R mutation showed a 3-fold decreased susceptibility to tenofovir in vitro [Chemington et al. *Interscience Conference on Antimicrobial Agents and Chemotherapy* 1997, 37th]. Notably, clinical HIV strains expressing the M184V lamivudine-associated resistance mutation on RT show wild-type or increased susceptibility to tenofovir in vitro, independent of changes in Ki for the mutant enzyme [Miller et al. *Interscience Conference on Antimicrobial Agents and Chemotherapy* 1998,]. Long-term treatment (5 to 15 weeks) of newborn rhesus macaques with tenofovir (doses of 30 mg/kg) starting 3 weeks after inoculation with simian immunodeficiency virus, resulted in emergence of SIV with approximately 5-fold decreased susceptibility to tenofovir [Van Rompay et al. *Antimicrobial Agents and Chemotherapy* 1996, 40:11 (2586-2591)]. This low level of resistance was associated with the appearance of the K65R mutation.

In a preferred embodiment, a combination is provided comprising (i) TMC278 or its stereoisomeric form or pharmaceutically acceptable salt or its prodrug, and (ii) tenofovir or its prodrug tenofovir disoproxil fumarate, wherein TMC278 and tenofovir or its prodrug tenofovir disoproxil fumarate are therapeutically effective HIV inhibitors at a dose that can be administered once daily.

In another preferred embodiment, a triple combination is provided comprising (i) TMC278 or its stereoisomeric form or pharmaceutically acceptable salt or its prodrug, and (ii) a nucleoside reverse transcriptase inhibitor, and (iii) tenofovir disoproxil fumarate; wherein TMC278 and the nucleoside reverse transcriptase inhibitor and tenofovir disoproxil fumarate are therapeutically effective HIV inhibitors at a dose that can be administered once daily.

Preferred nucleoside reverse transcriptase inhibitors that can be used in the combinations of this invention include abacavir or a pharmaceutically acceptable salt thereof, emtricitabine, racemic FTC and lamivudine (also named 3TC).

Emtricitabine or (−)-FTC is the left (−) rotatory enantiomeric form of racemic FTC or (±)-cis-4-amino-5-fluoro-1-[2-(hydroxymethyl)-1,3-oxathiolan-5-yl]-2(1H)-pyrimidinone (FTC). It is a commercially available nucleoside analogue and exhibits activity against HIV-1 [Hoong et al. *Journal of Organic Chemistry* 1992 (5563-5565); Jeong et al *Journal of Medicinal Chemistry* 1993, 36:2 (181-195); Van Roey et al. *Antiviral Chemistry and Chemotherapy* 1993, 4:6 (369-3751]. The in vitro anti-HIV-1 activity of (−)-beta-enantiomer of FTC was reported to be 20-fold more than the (+)-beta-enantiomer, and the (+)-enantiomer was significantly more toxic than the (−)-enantiomer to myeloid progenitor cells [Schinazi et al *Antimicrobial Agents and Chemotherapy* 1992, 36:11 (2423-2431)]. The potential for HIV-1 resistance to FTC was evaluated by serial passage of the virus in human PBMCs and MT-2 cells in the presence of increasing drug concentrations. Highly drug-resistant HIV-1 variants dominated the replicating virus population after two or more cycles of infection. RT derived from drug-resistant viral particles was 15- to 50-fold less susceptible to the 5′-triphosphate of FTC compared with the enzyme from parental drug susceptible virus. DNA sequence analysis of the RT gene amplified from resistant viruses consistently identified mutations at codon 184 from Met (ATG) to Val (GTG or GTA) [Schinazi et al *Antimicrobial Agents and Chemotherapy* 1993, 37:4 (875-881); Tisdale et al *Antiviral Research* 1993, 20: Suppl 1; Smith et al *Journal of Virology* 1997, 71:3 (2357-2362); Harrer et al *Journal of Infectious Diseases* 1996, 173:2 (476-479); Tisdale et al *Proceedings of the National Academy of Sciences of the United States of America* 1993, 90:12 (5653-5656)]. Due to this observed single mutation in the YMDD of reverse transcriptase in the HIV-infected patients, (−)-FTC is not suitable for monotherapy and needs to be administered in combination with other antiretroviral agents to effectively treat patients infected with HIV. Emtricitabine is available as 200 mg capsules to be taken once a day.

Lamivudine has the chemical name (−)-2′,3′-dideoxy-3′-thiacytidine and is described for instance in EP-382 526 as an antiviral nucleoside analogue. It is also a well established and useful antiretroviral which is commercially available for instance as 150 mg oral tablets. Lamivudine is also commercially available in combination with zidovudine (300 mg zidovudine/150 mg lamivudine), and in combination with lamivudine and abacavir sulfate (300 mg zidovudine/150 mg lamivudine/equivalent of 300 mg abacavir).

Abacavir is a well established and useful antiretroviral which is commercially available for instance as an oral solution of abacavir sulfate in a strength equivalent to 20 mg abacavir base/ml, or as an oral tablet of abacavir sulfate in a strength equivalent to 300 mg abacavir base. Abacavir sulfate is also commercially available in combination with lamivudine and zidovudine (300 mg zidovudine/150 mg lamivudine/equivalent of 300 mg abacavir).

Abacavir is a carbocyclic nucleoside with potent and selective anti-HIV activity. Abacavir in its optically active form is disclosed in EP-434 450. The cis-isomer of abacavir with unspecified absolute stereochemical configuration is described in EP-349 242. Abacavir is one of the most potent NRTI developed to date. An average reduction in viral load of more than 1.4 log 10 RNA copies/ml is observed after a short course of abacavir monotherapy. In vitro, resistant virus is not rapidly selected by abacavir. A significant decrease in susceptibility to abacavir in wild-type or zidovudine-resistant HIV-1 strains was not observed until after eight to ten passages in MT-4 cells. A set of resistance mutations at HIV reverse transcriptase (RT) codons, 65R, 74V, 115F and/or 184V, are selected during in vitro passage with abacavir, and a combination of these mutations was required to confer a 10-fold reduction in abacavir susceptibility in a laboratory strain of HIV. The first mutation detected upon passage of HIV-1 in an increasing concentration of abacavir is M184V, which confers only a 3-fold decrease in HIV-1 susceptibility. Phenotype resistance to 3TC and/or the presence of the 184V mutation does not prevent viral load response to abacavir therapy. Resistance to multiple nucleosides is associated with a decreased or absent response to abacavir [Kumar et al *Antimicrobial Agents and Chemotherapy* 1999, 43:3 (603-608); Lanier et al *International Conference on Retroviruses and Opportunistic Infections* 1998, 5th: Chicago; posted on 16 Apr. 1999].

In a preferred embodiment, a combination is provided comprising (i) TMC278 or a stereoisomeric form thereof; or a pharmaceutically acceptable salt thereof; or a prodrug thereof; and (ii) emtricitabine, wherein TMC278 and emtricitabine are therapeutically effective HIV inhibitors at a dose that can be administered once daily.

In a preferred embodiment, a combination is provided comprising (i) TMC278 or a stereoisomeric form thereof; or a pharmaceutically acceptable salt thereof; or a prodrug thereof; and (ii) lamivudine, wherein TMC278 and lamivudine are therapeutically effective HIV inhibitors at a dose that can be administered once daily.

In another preferred embodiment, a combination is provided comprising (i) TMC278 or a stereoisomeric form thereof; or a pharmaceutically acceptable salt thereof; or a prodrug thereof; and (ii) abacavir or a pharmaceutically acceptable salt thereof, characterized in that, TMC278 and abacavir are therapeutically effective HIV inhibitors at a dose that can be administered once daily.

In another preferred embodiment, a combination is provided comprising (i) TMC278 or a stereoisomeric form thereof; or a pharmaceutically acceptable salt thereof; or a prodrug thereof; and (ii) abacavir sulfate, characterized in that, TMC278 and abacavir sulfate are therapeutically effective HIV inhibitors at a dose that can be administered once daily.

In another preferred embodiment, a triple combination is provided comprising (i) TMC278 or a stereoisomeric form thereof; or a pharmaceutically acceptable salt thereof; or a prodrug thereof; and (ii) emtricitabine, and (iii) a nucleotide reverse transcriptase inhibitor, wherein TMC278 and the nucleotide reverse transcriptase inhibitor and emtricitabine are therapeutically effective HIV inhibitors at a dose that can be administered once daily.

In another preferred embodiment, a triple combination is provided comprising (i) TMC278 or or a stereoisomeric form thereof; or a pharmaceutically acceptable salt thereof; or a prodrug thereof; and (ii) lamivudine, and (iii) a nucleotide reverse transcriptase inhibitor, wherein TMC278 and the nucleotide reverse transcriptase inhibitor and lamivudine are therapeutically effective HIV inhibitors at a dose that can be administered once daily.

In another preferred embodiment, a triple combination is provided comprising (i) TMC278 or or a stereoisomeric form thereof; or a pharmaceutically acceptable salt thereof; or a prodrug thereof; and (ii) abacavir or a pharmaceutically acceptable salt thereof, or preferably abacavir sulfate, and (iii) a nucleotide reverse transcriptase inhibitor, wherein TMC278 and the nucleotide reverse transcriptase inhibitor and abacavir or a pharmaceutically acceptable salt thereof, or preferably abacavir sulphate, are therapeutically effective HIV inhibitors at a dose that can be administered once daily.

In another preferred embodiment, a triple combination is provided comprising (i) TMC278 or or a stereoisomeric form thereof; or a pharmaceutically acceptable salt thereof; or a prodrug thereof; and (ii) emtricitabine, and (iii) tenofovir or its prodrug tenofovir disoproxil fumarate, wherein TMC278 and emtricitabine and tenofovir or its prodrug tenofovir disoproxil fumarate are therapeutically effective HIV inhibitors at a dose that can be administered once daily.

In another preferred embodiment, a triple combination is provided comprising (i) TMC278 or a stereoisomeric form thereof; or a pharmaceutically acceptable salt thereof; or a prodrug thereof; and (ii) lamivudine and (iii) tenofovir or its prodrug tenofovir disoproxil fumarate, wherein TMC278 and lamivudine and tenofovir or its prodrug tenofovir disoproxil fumarate are therapeutically effective HIV inhibitors at a dose that can be administered once daily.

In another preferred embodiment, a triple combination is provided comprising (i) TMC278 or a stereoisomeric form thereof; or a pharmaceutically acceptable salt thereof; or a prodrug thereof; and (ii) abacavir or a pharmaceutically acceptable salt form thereof, preferably abacavir sulfate; and (iii) tenofovir or its prodrug tenofovir disoproxil fumarate, wherein TMC278 and abacavir or a pharmaceutically acceptable salt form thereof, preferably abacavir sulfate and tenofovir or its prodrug tenofovir disoproxil fumarate are therapeutically effective HIV inhibitors at a dose that can be administered once daily.

The following preferred triple combinations are also included
(a) TMC278 or a stereoisomeric form thereof; or a pharmaceutically acceptable salt thereof; or a prodrug thereof; with emtricitabine and tenofovir disoproxil fumarate;
(b) TMC278 or a stereoisomeric form thereof; or a pharmaceutically acceptable salt thereof; or a prodrug thereof; with lamivudine and tenofovir disoproxil fumarate.
(c) TMC278 or a stereoisomeric form thereof; or a pharmaceutically acceptable salt thereof; or a prodrug thereof; with abacavir sulfate and tenofovir disoproxil fumarate.
(d) TMC278 or a stereoisomeric form thereof; or a pharmaceutically acceptable salt thereof; or a prodrug thereof; with emtricitabine and lamivudine;
(e) TMC278 or a stereoisomeric form thereof; or a pharmaceutically acceptable salt thereof; or a prodrug thereof; emtricitabine and abacavir or a pharmaceutically acceptable salt thereof, preferably abacavir sulfate.
(f) TMC278 or a stereoisomeric form thereof; or a pharmaceutically acceptable salt thereof; or a prodrug thereof; abacavir or a pharmaceutically acceptable salt thereof, preferably abacavir sulfate and lamivudine.

In particular, in each of the combinations (a)-(f) the active ingredients, in particular TMC278, emtricitabine, lamivudine, abacavir or a pharmaceutically acceptable salt form thereof, preferably abacavir sulfate, and tenofovir or its prodrug tenofovir disoproxil fumarate, are therapeutically effective HIV inhibitors at a dose that can be administered once daily.

The double combinations of the present invention may contain one or more additional active ingredients, which can be agents useful for treating HIV infected patients or other active agents. The triple combinations of the present invention may equally contain one or more additional active ingredients, which can be agents useful for treating HIV infected patients or other active agents. Preferably any of these additional agents are therapeutically effective at a dose that can be administered once daily.

The active ingredients of the combinations of the present invention may be administered simultaneously, concurrently or sequentially. Simultaneous administration may be done by employing a unitary pharmaceutical formulation or separate pharmaceutical formulations. In general, the combinations may be administered by topical, oral, rectal, intravenous, subcutaneous or intramuscular routes. For first line therapy of HIV infection, simultaneous administration employing a unitary pharmaceutical formulation is preferred.

Thus, in another aspect there is provided a product containing a combination as specified herein as a combined preparation for simultaneous, separate or sequential use against HIV infection.

The invention also provides a product containing (i) TMC278 or a stereoisomeric form thereof; or a pharmaceutically acceptable salt thereof; or a prodrug thereof; and (ii) a nucleoside reverse transcriptase inhibitor and/or a nucleotide reverse transcriptase inhibitor; wherein TMC278 and the nucleotide reverse transcriptase inhibitor and/or the nucleoside reverse transcriptase inhibitor are therapeutically effective HIV inhibitors at a dose that can be administered once daily; as a combined preparation for simultaneous, separate or sequential use against HIV infection.

In a further aspect there is provided a product containing (i) TMC278 or a stereoisomeric form thereof; or a pharmaceutically acceptable salt thereof; or a prodrug thereof; and (ii) a nucleoside reverse transcriptase inhibitor; wherein TMC278 and the nucleoside reverse transcriptase inhibitor are therapeutically effective HIV inhibitors at a dose that can be administered once daily; as a combined preparation for simultaneous, separate or sequential use against HIV infection.

In another aspect there is provided a product containing (i) TMC278 or a stereoisomeric form thereof; or a pharmaceutically acceptable salt thereof; or a prodrug thereof; and (ii) a nucleotide reverse transcriptase inhibitor, wherein TMC278 and the nucleotide reverse transcriptase inhibitor are therapeutically effective HIV inhibitors at a dose that can be administered once daily; as a combined preparation for simultaneous, separate or sequential use against HIV infection.

In another aspect there is provided a product containing (i) TMC278 or a stereo-isomeric form thereof; or a pharmaceutically acceptable salt thereof; or a prodrug thereof; and (ii) a nucleoside reverse transcriptase inhibitor; and (iii) a nucleotide reverse transcriptase inhibitor; wherein TMC278 and the nucleotide reverse transcriptase inhibitor and the nucleoside reverse transcriptase inhibitor are therapeutically effective HIV inhibitors at a dose that can be administered once daily; as a combined preparation for simultaneous, separate or sequential use against HIV infection.

In another aspect there is provided a product containing (i) TMC278 or a stereoisomeric form thereof; or a pharmaceutically acceptable salt thereof; or a prodrug thereof; and (ii) a nucleoside reverse transcriptase inhibitor; and (iii) a second nucleoside reverse transcriptase inhibitor other than the nucleoside reverse transcriptase inhibitor of (ii); wherein TMC278 and the nucleoside reverse transcriptase inhibitors are therapeutically effective HIV inhibitors at a dose that can be administered once daily; as a combined preparation for simultaneous, separate or sequential use against HIV infection.

The active ingredients in the products of the invention are present in therapeutically effective amounts, the latter meaning an amount that is sufficient to exert a sufficient HIV inhibitory effect during a certain time period, i.e. the time period between each intake of the formulations, preferably for about 24 hours.

Particular embodiments are products as specified above containing one or more of the specific active ingredients mentioned herein such as emtricitabine, racemic FTC, lamivudin, tenofovir and its prodrug tenofovir disoproxil fumarate.

The products as mentioned above may contain separate formulations of the active ingredients, or two or where applicable more of the active ingredients may be co-formulated.

In still a further aspect the invention provides pharmaceutical formulations containing a combination as specified herein and a suitable carrier.

In another aspect there is provided a pharmaceutical formulation comprising a pharmaceutically acceptable carrier and as active ingredients (i) TMC278 or a stereoisomeric form thereof; or a pharmaceutically acceptable salt thereof; or a prodrug thereof; and (ii) a nucleoside reverse transcriptase inhibitor and/or a nucleotide reverse transcriptase inhibitor; wherein TMC278 and the nucleoside reverse transcriptase inhibitor and/or the nucleotide reverse transcriptase inhibitor are therapeutically effective HIV inhibitors at a dose that can be administered once daily.

The invention further provides a pharmaceutical formulation comprising a pharmaceutically acceptable carrier and as active ingredients (i) TMC278 or a stereoisomeric form thereof; or a pharmaceutically acceptable salt thereof; or a prodrug thereof; and (ii) a nucleoside reverse transcriptase inhibitor; wherein TMC278 and the nucleoside reverse transcriptase inhibitor are therapeutically effective HIV inhibitors at a dose that can be administered once daily.

In still another aspect there is provided a pharmaceutical formulation comprising a pharmaceutically acceptable carrier and as active ingredients (i) TMC278 or a stereoisomeric form thereof; or a pharmaceutically acceptable salt thereof; or a prodrug thereof; and (ii) a nucleotide reverse transcriptase inhibitor, wherein TMC278 and the nucleoside reverse transcriptase inhibitor and the nucleotide reverse transcriptase inhibitor are therapeutically effective HIV inhibitors at a dose that can be administered once daily.

In still another aspect there is provided a pharmaceutical formulation comprising a pharmaceutically acceptable carrier and as active ingredients (i) TMC278 or a stereoisomeric form thereof; or a pharmaceutically acceptable salt thereof; or a prodrug thereof; and (ii) a nucleoside reverse transcriptase inhibitor; and (iii) a nucleotide reverse transcriptase inhibitor; wherein TMC278 and the nucleoside reverse transcriptase inhibitor and the nucleotide reverse transcriptase inhibitors are therapeutically effective HIV inhibitors at a dose that can be administered once daily.

In still another aspect there is provided a pharmaceutical formulation comprising a pharmaceutically acceptable carrier and as active ingredients (i) TMC278 or a stereoisomeric form thereof; or a pharmaceutically acceptable salt thereof; or a prodrug thereof; and (ii) a nucleoside reverse transcriptase inhibitor; and (iii) a second nucleoside reverse transcriptase inhibitor different from the nucleoside reverse transcriptase inhibitor of (ii); wherein TMC278 and the nucleoside reverse transcriptase inhibitors are therapeutically effective HIV inhibitors at a dose that can be administered once daily.

The active ingredients in the pharmaceutical formulations of the invention are present in therapeutically effective amounts, the latter meaning an amount that is sufficient to exert a sufficient HIV inhibitory effect during a certain time period, i.e. the time period between each intake of the formulations, preferably for about 24 hours.

Particular embodiments are pharmaceutical formulations as specified above containing one or more of the specific active ingredients mentioned herein such as emtricitabine, racemic FTC, lamivudin, tenofovir and its prodrug tenofovir disoproxil fumarate.

The pharmaceutical formulations of the present invention may be formulated into various forms for different types of administration. To prepare the pharmaceutical formulations of this invention, effective amounts of the active ingredients, optionally in addition salt form, is combined in intimate admixture with a pharmaceutically acceptable carrier, which carrier may take a wide variety of forms depending on the form of preparation desired for administration. The pharmaceutical formulations of the invention are preferably formulated in unitary dosage form suitable, particularly, for administration orally, rectally, percutaneously, or by parenteral injection. For example, in preparing the formulations in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

In one aspect of the invention, the present combinations can be formulated in an oral tablet form further comprising pharmaceutically acceptable excipients having a weight ranging between 150 mg and 600 mg, suitable ranging between 200 and 400 mg. Convenient oral tablet forms containing the active ingredients according to the present invention have a total nominal weight ranging between 200 mg and 1500 mg, suitably between 500 mg and 1250 mg, more suitable between 600 and 1100 mg.

An advantage of the pharmaceutical formulations of the invention resides in the fact that each of the ingredients of the present combinations can be co-formulated in one pharmaceutical formulation and do not have to be administered separately. The daily therapeutic antiretroviral amount of the ingredients of the present combinations of such co-formulated single pharmaceutical form preferably is administered in a single unit dosage form but, if desired, also multiple unit dosage forms, such as two, three, four, five or even more unit dosage forms may be administered. A physician will be able to determine the exact dosage to be given taking into account the severity of the patient's condition as well as the patient's weight, gender and possibly other parameters such as individual differences in absorption, biodistribution, metabolism and excretion rates for each drug as well as other factors known to those skilled in the art.

This invention also provides a method of treating HIV infected patients said method comprising administering a combination as specified herein.

Furthermore there is provided a method of treating HIV infected patients, said method comprising administering TMC278 or its stereoisomeric form or pharmaceutically acceptable salt or its prodrug, in combination with a nucleoside reverse transcriptase inhibitor and/or a nucleotide reverse transcriptase inhibitor, in which method a therapeutically effective amount of TMC278 and the nucleoside reverse transcriptase inhibitor and/or nucleotide reverse transcriptase inhibitor can be administered once daily.

Furthermore there is provided a method of treating HIV infected patients, said method comprising administering TMC278 or its stereoisomeric form or pharmaceutically acceptable salt or its prodrug, in combination with a nucleoside reverse transcriptase inhibitor, in which method a therapeutically effective amount of TMC278 and the nucleoside reverse transcriptase inhibitor can be administered once daily.

In a further aspect of this invention concerns a method of treating HIV infected patients said method comprising administering TMC278 or its stereoisomeric form or pharmaceutically acceptable salt or its prodrug, and a nucleotide reverse transcriptase inhibitor, in which method a therapeutically effective amount of TMC278 and the nucleotide reverse transcriptase inhibitor can be administered once daily.

Still a further aspect of this invention comprises a method of treating HIV infected patients said method comprising administering TMC278 or its stereoisomeric form or pharmaceutically acceptable salt or its prodrug, in combination with a nucleoside reverse transcriptase inhibitor, and a nucleotide reverse transcriptase inhibitor, in which method a therapeutically effective amount of TMC278, the nucleotide reverse transcriptase inhibitor and the nucleoside reverse transcriptase inhibitor can be administered once daily.

Still a further aspect of this invention comprises a method of treating HIV infected patients said method comprising administering TMC278 or its stereoisomeric form or pharmaceutically acceptable salt or its prodrug, in combination with a nucleoside reverse transcriptase inhibitor, and a second nucleoside reverse transcriptase inhibitor different from the former nucleoside reverse transcriptase inhibitor, in which method a therapeutically effective amount of TMC278, the nucleoside reverse transcriptase inhibitors can be administered once daily.

The active ingredients in the methods of the invention are administered in therapeutically effective amounts, the latter meaning an amount that is sufficient to exert a sufficient HIV inhibitory effect during a certain time period, i.e. the time period between each intake of the formulations, preferably for about 24 hours.

Particular embodiments are methods as specified above wherein one or more of the specific active ingredients mentioned herein such as emtricitabine, racemic FTC, lamivudin, tenofovir and its prodrug tenofovir disoproxil fumarate, are administered.

One embodiment of the present invention relates to the present combinations for use as a medicine. Another embodiment relates to the combinations of the present invention for use in the manufacture of a medicament to treat HIV infected patients.

Of particular interest are any of the combinations as specified herein, or any of the products, pharmaceutical formulations, unit dosage forms, methods and uses being based on said combinations, wherein TMC278 is E-TMC287, or preferably TMC278 hydrochloride salt or more preferably E-TMC278 hydrochloride salt.

The combinations of this invention are especially useful for the treatment of AIDS and related clinical conditions such as AIDS related complex (ARC), progressive generalised lymphadenopathy (PGL) or AIDS related neurological conditions such as multiple sclerosis. The present triple combination may be particularly useful for the treatment of drug-naïve HIV infected patients.

The combinations of the invention are also useful for the prevention of HIV transmission or infection in humans, in particular sexual transmission. Thus, the present invention relates to the use of combinations according to the present invention for the manufacture of a medicament for the prevention of HIV infection or transmission via sexual intercourse or related intimate contact between partners. The invention also relates to a method of preventing HIV infection or transmission via sexual intercourse or related intimate contact between partners comprising administering to a subject in need thereof an effective amount of any of the combinations according to the present invention.

The respective daily dose for each of the active ingredients of a combination according to the present invention may range between 10 mg and 800 mg, preferably between 50 and 400 mg, more preferably between 50 and 300 mg, or between 100 and 300 mg. In particular, the daily dose for TMC278 may range between 10 mg and 500 mg, preferably between 10 and 300, more preferably between 50 and 250 mg, still more preferably between 50 and 200 mg, e.g. about 100 mg.

The weight ratio of each couple of components of the triple combination taken on a daily basis may vary in a range from 1/10 to 10/1. Suitably, the weight ratio of each couple varies between 1/6 and 6/1, more suitably 1/4 and 4/1, preferably between 1/3 and 3/1, and more preferably between 1/2 and 2/1.

Table 2 lists some examples of the daily dose for each of the active ingredients in combinations of compound E-TMC278, emtricitabine and tenofovir.

| Combination no. | E-TMC278 | Emtricitabine | Tenofovir |
|---|---|---|---|
| 1 | 50 mg | 200 mg | — |
| 2 | 50 mg | — | 300 mg |
| 3 | 100 mg | 200 mg | — |
| 4 | 100 mg | — | 300 mg |
| 5 | 200 mg | 200 mg | — |
| 6 | 200 mg | — | 300 mg |
| 7 | 50 mg | 200 mg | 300 mg |
| 8 | 100 mg | 200 mg | 300 mg |
| 9 | 200 mg | 200 mg | 300 mg |

Table 3 lists some examples of the daily dose for each of the active ingredients in combinations of TMC278, abacavir and lamivudine wherein the dose mentioned in the table for abacavir sulfate is the equivalent dose of abacavir base.

| Combination no. | E-TMC278 | Lamivudine | Abacavir sulfate |
|---|---|---|---|
| 1 | 50 mg | 150 mg | 300 mg |
| 2 | 100 mg | 150 mg | 300 mg |
| 3 | 200 mg | 150 mg | 300 mg |

Thus, an interesting combination according to the present invention comprises compound E-(A) in a daily dose ranging between 10 mg and 500 mg, a daily dose of 150 mg lamivudine and a daily dose of an equivalent of 300 mg abacavir base. Suitably, such combination is formulated in a single pharmaceutical form.

Another interesting combination according to the present invention comprises compound E-(A) in a daily dose ranging between 50 mg and 250 mg, a daily dose of 150 mg lamivudine and a daily dose of an equivalent of 300 mg abacavir base. Suitably, such combination is formulated in a single pharmaceutical form.

The present invention also relates to a pharmaceutical composition in a form adapted to be applied to a site where sexual intercourse or related intimate contact can take place, such as the genitals, rectum, mouth, hands, lower abdomen, upper thighs, especially the vagina and mouth, comprising a pharmaceutically acceptable carrier and as active ingredients an effective amount of a combination according to the present invention. As appropriate special adapted compositions there may be cited all compositions usually employed for being applied to the vagina, rectum, mouth and skin such as for example gels, jellies, creams, ointments, films, sponges, foams, intravaginal rings, cervical caps, suppositories for rectal or vaginal application, vaginal or rectal or buccal tablets, mouthwashes. To prepare such pharmaceutical compositions, an effective amount of each of the particular compounds of the triple combination as the active ingredients is combined in intimate admixture with a pharmaceutically acceptable carrier, which carrier may take a wide variety of forms depending on the form of administration. In order to increase the residence time of such pharmaceutical composition at the site of administration, it may be advantageous to include in the composition a bioadhesive, in particular a bioadhesive polymer. A bioadhesive may be defined as a material that adheres to a live biological surface such as for example a mucus membrane or skin tissue.

Thus, the present invention also relates to a pharmaceutical composition comprising a pharmaceutically acceptable carrier and as active ingredients an effective amount of each of the compounds of the present triple combination characterized in that the pharmaceutical composition is bioadhesive to the site of application. Preferably, the site of application is the vagina, rectum, mouth or skin, most preferred is the vagina.

Otten R A et al in Journal of Virology (2000), 74(20), 9771-9775 and Witvrouw M et al in Antiviral Research (2000), 46(3), 215-221 disclose the ability of tenofovir to delay HIV viral breakthrough after high-risk sexual exposure.

Pani A et al in Antiviral Chemistry & Chemotherapy (2001), 12(Suppl. 1), 51-59 describe the ability of lamivudine to delay viral breakthrough.

The ability of TMC278 to prevent HIV infection via sexual intercourse or related intimate contact between partners can be demonstrated in the following test. Immature monocyte derived dendritic cells (immMO-DC) represent a good model for interstitial dendritic cells, which are early targets during sexual HIV transmission and important initiators of the immune response. These immMO-DC were used in "in vitro" models to test the prevention of HIV infection via sexual intercourse or related intimate contact between partners. One such model is described in the experimental part and indicates that the TMC278 potently inhibits HIV replication in MO-DC/CD4(+) T cell co-cultures.

EXAMPLES

Example 1

Pharmacokinetics of E-TMC278

A double-blind, randomized, placebo-controlled Phase I trial was designed to evaluate safety, tolerability, and ex-vivo pharmacokinetics of single doses of compound E-TMC278 in healthy male volunteers. Oral doses of 12.5, 25, and 50 mg were formulated in PEG 400 and taken with a standard meal. The pharmacokinetic results are shown in Table 4.

The pharmacokinetic results of another double-blind, randomized, placebo-controlled Phase I study with 4 dosing sessions to evaluate the safety, tolerability, pharmacokinetics and ex-vivo pharmacodynamics of single 100 mg and 200 mg oral doses of compound E-TMC278 in healthy male subjects are also reported in Table 4. Randomization was such that for each session 6 subjects received the same dose of compound E-TMC278 and 3 subjects received placebo. There was a time interval of about 14 days between each dosing session Table 4 shows that high and dose-proportional exposures were obtained. The correlation coefficient for the 5 $C_{max}$ datapoints is 0.9897 and for the area under the curve values between 0 and 48 hours ($AUC_{0-48}$ hr) 0.9952. Half-life of plasma concentrations ranged between 37 and 39 hours. The compound was well tolerated by the volunteers. No relevant adverse effects of the drug were noted.

TABLE 4

| Parameter | 12.5 mg | 25 mg | 50 mg | 100 mg | 200 mg |
|---|---|---|---|---|---|
| $C_{max}$ (ng/ml) | 73 ± 14 | 149 ± 32 | 267 ± 27 | 482 ± 121 | 807 ± 207 |
| $T_{max}$ (hr) | 4.0 ± 0 | 4.0 ± 1.3 | 4.0 ± 1.3 | 4.3 ± 0.8 | 4.3 ± 0.8 |
| $AUC_{0-48\,hr}$ (nghr/ml) | 1337 ± 310 | 2805 ± 496 | 5094 ± 509 | 8162 ± 2251 | 15592 ± 2746 |

TABLE 4-continued

| Parameter | 12.5 mg | 25 mg | 50 mg | 100 mg | 200 mg |
|---|---|---|---|---|---|
| $AUC_{0-\infty}$ (nghr/ml) | 2210 ± 473 | 4637 ± 1164 | 8872 ± 1342 | 15844 ± 4592 | |
| $T_{1/2}$ (hr) | 37.1 | 38.7 | 45 ± 9 | 55 ± 18 | |

Example 2

Virological Profile of Compound E-TMC278

Compound E-TMC278 was tested in a cell-based assay, using natural host cells of HIV. MT-4 cells (a cell line of human T cells) were infected with HIV-1 (wild type or mutants) and exposed to different concentrations of antiviral compound in the presence of 10% fetal calf serum. Cytotoxicity was determined in parallel with the antiviral activity so that the selectivity of the antiviral effect could be assessed. Active compounds have to penetrate the cell membrane in order to interfere with replication steps inside the cell.

After four days of incubation at 37° C., the viability of the HIV and mock-infected cells was assessed by an automated tetrazolium-based calorimetric assay. This method enabled the calculation of both the 50% inhibitory concentration for inhibition of viral cytopathicity (IC50), the IC90, and the 50% cytotoxic concentration (CC50). The ratio CC50/IC50, also called the selectivity index, is an indication of the specificity of the antiviral effect. Tested HIV strains included: Wild type (wt) HIV-1; a panel of single and double mutants, obtained by site-directed mutagenesis (SDM), and a panel of clinical isolates, selected for resistance against NNRTIs.

Activity Towards Wild Type and SDM Mutants

A limited panel of HIV-1 mutants was constructed using site-directed mutagenesis (SDM) and homologous recombination techniques. Compound E-TMC278 was tested against an extended panel of single and double mutants known to be resistant against commercially available NNRTIs. Nevirapine (NVP) and efavirenz (EFV) were included as controls.

The results are shown in Table 5 (values presented are IC50 values in nM). For wild type virus, the obtained IC50 was 0.4 nM (0.15 ng/ml) and the IC90 1.3 nM (0.48 ng/ml). The HIV strain with the lowest sensitivity against compound E-TMC278 within this selection was the double mutant 100I+103N, with an IC50 of about 8 nM and an IC90 of about 16 nM.

TABLE 5

| | NVP | EFV | Compound E-TMC278 |
|---|---|---|---|
| wild type | 81 | 1.4 | 0.4 |
| 100I | 597 | 35 | 0.4 |
| 101E | 547 | 5 | 1.6 |
| 103N | 2,879 | 28 | 0.3 |
| 106A | 2,983 | 23 | 0.2 |
| 108I | — | 2 | 0.3 |
| 138K | 64 | 1.3 | 0.4 |
| 179D | 161 | 6 | 0.6 |
| 179E | 158 | 5 | 0.4 |
| 181C | 10,000 | 2 | 1.3 |
| 188C | 3,764 | 5 | 0.1 |
| 188H | 241 | 9 | 0.2 |
| 188L | 10,000 | 78 | 2.0 |
| 190A | 4,101 | 8 | 0.3 |
| 190S | 10,000 | 275 | 0.1 |
| 225H | 171 | 2 | 0.3 |
| 227C | 1,816 | 36 | 2.0 |
| 227L | 78 | 0.3 | 0.3 |
| 234I | 45 | NT | 0.3 |
| 236L | 41 | 1 | 0.3 |
| 100I + 103N | 10,000 | 10,000 | 7.9 |
| 101E + 103N | 7,033 | 84 | 0.5 |
| 103N + 181I | 10,000 | 37 | 1.0 |
| 227L + 106A | 10,000 | 8 | 1.0 |

Development of Resistance In Vitro

NNRTIs are highly selective inhibitors of HIV-1 but their current clinical use is limited by the rapid emergence of NNRTI (cross-) resistance. The rate of resistance emergence against compound E-TMC278 and the first generation NNRTIs nevirapine and efavirenz was compared in vitro.

MT4 cells were infected with wild type HIV-1 at high multiplicity of infection (>1 infectious virus per cell, to maximize the genetic diversity of the virus population) in the presence of various concentrations of compound E-TMC278 (40, 200, 1000 and 5000×IC50), and were monitored twice a week for virus replication. Emerging virus was collected for pheno- and genotyping. Cultures without evidence of virus replication were further sub-cultivated in the presence of the same concentration of inhibitor for a total duration of 30 days (10 passages).

Resistance to nevirapine emerged within 3-6 days, at all tested concentrations. Breakthrough virus harboured the typical Y181C mutation. The same experiments with efavirenz resulted in the selection of G190E at all concentrations (up to 5 μM) within 3 to 7 days. Compound E-TMC278 did not select for resistant virus within 30 days using wild-type virus. If a double resistant mutant K103N+Y181C (IC50 0.8 nM) was used instead of wild type virus, resistance did emerge at all tested concentrations. Starting from the single mutants Y181C (IC50 1.3 nM) or 103N (IC50 0.3 nM), virus breakthrough did not occur at 40 and 200 nM, but did occur at 10 nM.

In this experimental setting of high genetic diversity, HIV-1, resistant to first generation NNRTIs, was selected very rapidly. Resistant viruses harboured only one mutation. In contrast, emergence of HIV-1, resistant to compound E-TMC278 was delayed or did not occur.

Cardiovascular and Pulmonary Safety of Compound E-TMC278

Compound E-TMC278 had little or no effect on cardiovascular and pulmonary parameters in vivo at plasma levels covering and exceeding the targeted plasma levels in man and at concentrations in vitro covering or exceeding the anti-viral concentration in vitro.

Example 3

In Vitro Models to Test the Ability of Compound E-TMC278 to Prevent HIV Infection Via Sexual Intercourse or Related Intimate Contact Between Partners For instance, in one model, monocyte-derived dendritic cells (MO-DC) were infected for 2-hours with the monotropic HIV strain Ba-L at a multiplicity of infection (MOI) of $10^{-3}$. After infection, cells were washed 6 times and resuspended in 10% BCS at 400.000 cells/ml. Autologous CD4(+) T cells were purified out of the lymphocyte fraction of the same elutration as the MO-DC and used at a concentration of $2\times10^6$ cells/ml ((ratio MO-DC/CD4(+) T: 1/5).

A serial dilution of a compound of formula (I) (test compound) was added to the MO-DC/CD4(+) T cell co-cultures. Each experiment was done in 96-well plates, in which each cup contained 50 µl of MO-DC, 50 µl of CD4(+) T cells and 100 µl of test compound. Half of the culture medium, with test compound, was refreshed twice weekly. Supernatants were analysed in ELISA after 14 days of culture. To determine antiviral activity, the test compound concentration able to suppress 50% of the viral replication at the end of the primary cultures (EC50) was measured. For compound E-TMC278, the EC50 value was 0.55 nM.

Example 4

Formulations

Tablet formulation of the following composition:

| | |
|---|---|
| Emtricitabine | 300 mg |
| Tenofovir diisoproxyl fumarate | 300 mg |
| E-TMC278 hydrochloride salt | 110 mg |
| HPMC 2910 15 mPa · s | 24 mg |
| Polysorbate 20 | 6 mg |
| Crosspolyvidone | 18 mg |
| Lactose monohydrate | 43 mg |
| Magnesium stearate | 3 mg |
| Talcum | 6 mg |

The active ingredients and lactose are fluidised and sprayed with a solution of HPMC and polysorbate in water (at an equivalent of 120 ml/tablet). Subsequently crosspolyvidone is added, while still being fluidised, followed by magnesium stearate and talcum. The thus obtained granulate is compressed into 13 mm cylindrical tablets using standard compressing equipment.

The invention claimed is:

1. A combination comprising
   (i) 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof, and
   (ii) tenofovir or its prodrug tenofovir disoproxil fumarate, and
   (iii) emtricitabine;
   wherein the 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof; the tenofovir or its prodrug tenofovir disoproxil fumarate; and the emtricitabine are therapeutically effective HIV inhibitors at a dose that can be administered once daily.

2. The combination according to claim 1, wherein the 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof, is E-4-[[4-[[4-(2-cyanoethenyl)-2,6-dimethylphenyl]-amino]-2-pyrimidinyl]-amino]-benzonitrile.

3. The combination of claim 1, wherein the 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof, is E-4-[[4-[[4-(2-cyanoethenyl)-2,6-dimethylphenyl]-amino]-2-pyrimidinyl]-amino]-benzonitrile hydrochloride.

4. The combination of claim 1, wherein the 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof, is 4-[[4-[[4-(2-cyanoethenyl)-2,6-dimethylphenyl]-amino]-2-pyrimidinyl]-amino]-benzonitrile hydrochloride.

5. The combination of claim 1, comprising tenofovir disoproxil fumarate.

6. The combination of claim 3, comprising tenofovir disoproxil fumarate.

7. The combination of claim 1 comprising between 10 mg and 500 mg of the 4-[[4-[[4-(2-cyanoethenyl)-2,6-dimethylphenyl]-amino]-2-pyrimidinyl]-amino]-benzonitrile or a stereoisomeric form thereof.

8. The combination of claim 1 comprising between 10 mg and 300 mg of the 4-[[4-[[4-(2-cyanoethenyl)-2,6-dimethylphenyl]-amino]-2-pyrimidinyl]-amino]-benzonitrile or a stereoisomeric form thereof.

9. The combination of claim 1 comprising about 25 mg of the 4-[[4-[[4-(2-cyanoethenyl)-2,6-dimethylphenyl]-amino]-2-pyrimidinyl]-amino]-benzonitrile or a stereoisomeric form thereof.

10. The combination of claim 1, wherein the 4-[[4-[[4-(2-cyanoethenyl)-2,6-dimethylphenyl]-amino]-2-pyrimidinyl]-amino]-benzonitrile, or a stereoisomeric form thereof; or a pharmaceutically acceptable salt thereof, tenofovir or its prodrug tenofovir disoproxil fumarate; and emtricitabine are together in a unitary pharmaceutically acceptable formulation.

11. The combination of claim 10, wherein the pharmaceutically acceptable formulation is selected from the group consisting of tablets, capsules, parenteral compositions, injectable solutions, and injectable suspensions.

12. The combination of claim 11, wherein the pharmaceutically acceptable formulation is a tablet.

13. The combination of claim 3, wherein the E-4-[[4-[[4-(2-cyanoethenyl)-2,6-dimethylphenyl]-amino]-2-pyrimidinyl]-amino]-benzonitrile hydrochloride, tenofovir or its prodrug tenofovir disoproxil fumarate, and emtricitabine are together in a unitary pharmaceutically acceptable formulation.

14. The combination of claim 13, wherein the pharmaceutically acceptable formulation is a tablet.

15. The combination of claim 6, wherein the E-4-[[4-[[4-(2-cyanoethenyl)-2,6-dimethylphenyl]-amino]-2-pyrimidinyl]-amino]-benzonitrile hydrochloride, tenofovir disoproxil fumarate, and emtricitabine are together in a unitary pharmaceutically acceptable formulation.

16. The combination of claim 15, wherein the pharmaceutically acceptable formulation is a tablet.

17. A method of treating HIV infection in a patient comprising administering to the patient the combination of claim 1 once daily.

18. A method of treating HIV infection in a patient comprising administering to the patient the combination of claim 10 once daily.

19. A method of treating HIV infection in a patient comprising administering to the patient the combination of claim 15 once daily.

20. A method of treating HIV infection in a patient comprising administering to the patient the combination of claim 16 once daily.

21. A pharmaceutical formulation comprising the combination of claim 1 and a pharmaceutically acceptable carrier.

22. The pharmaceutical formulation of claim 21, wherein the formulation is selected from the group consisting of tablets, capsules, parenteral compositions, injectable solutions, and injectable suspension.

23. The pharmaceutical formulation of claim 22, wherein the formulation is a tablet.

24. A pharmaceutical formulation comprising the combination of claim 3 and a pharmaceutically acceptable carrier.

25. The pharmaceutical formulation of claim 24, wherein the formulation is a tablet.

26. A pharmaceutical formulation comprising the combination of claim 6 and a pharmaceutically acceptable carrier.

27. The pharmaceutical formulation of claim 26, wherein the formulation is a tablet.

28. A method of treating HIV infection in a patient comprising administering to the patient the pharmaceutical formulation of claim 21 once daily.

29. A method of treating HIV infection in a patient comprising administering to the patient the pharmaceutical formulation of claim 26 once daily.

30. A method of treating HIV infection in a patient comprising administering to the patient the pharmaceutical formulation of claim 27 once daily.

31. A kit comprising the combination of claim 1 packaged with instructions for use.

32. A kit comprising the combination of claim 3 packaged with instructions for use.

33. A kit comprising the combination of claim 6 packaged with instructions for use.

* * * * *